US00PP37061P2

(12) United States Plant Patent
Carrella

(10) Patent No.: US PP37,061 P2
(45) Date of Patent: Oct. 21, 2025

(54) ***CALIBRACHOA* PLANT NAMED 'KLECA23987'**

(50) Latin Name: *Calibrachoa sp.*
Varietal Denomination: KLECA23987

(71) Applicant: KLEMM + SOHN GMBH & CO. KG, Stuttgart (DE)

(72) Inventor: Angelo Carrella, Palma Campania (IT)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/988,305

(22) Filed: Dec. 19, 2024

(51) Int. Cl.
*A01H 6/82* (2018.01)
*A01H 5/02* (2018.01)

(52) U.S. Cl.
USPC ..... Plt./413

(58) Field of Classification Search
USPC ..... Plt./413
CPC ..... A01H 6/821; A01H 5/02
See application file for complete search history.

*Primary Examiner* — Keith O. Robinson
(74) *Attorney, Agent, or Firm* — Weatherly IP Solutions, LLC; James Weatherly

(57) ABSTRACT

A new *Calibrachoa* plant particularly distinguished by having a yellow flower with red veins and a red magenta border; and a mounding plant habit, is disclosed.

1 Drawing Sheet

Genus and species: *Calibrachoa sp.*
Variety denomination: 'KLECA23987'.

BACKGROUND OF THE NEW PLANT

The present invention comprises a new and distinct variety of *Calibrachoa,* botanically known as *Calibrachoa* sp., and hereinafter referred to by the variety name 'KLECA23987'. 'KLECA23987' originated from a controlled-cross between the female *Calibrachoa* variety 'KLECA20803' (U.S. Plant Pat. No. 33,988) and the male *Calibrachoa* variety 'KLECA22825' (unpatented).

In August 2019, two *Calibrachoa* parental lines, the female variety 'KLECA20803' and the male variety 'KLECA22825', were crossed via a controlled-cross in Stuttgart, Germany and seeds were obtained. The seeds were sown and plants were grown for evaluation. A plant line was selected in May 2020 and subsequently named 'KLECA23987'. In May 2020, 'KLECA23987' was first vegetatively propagated by cuttings. 'KLECA23987' was found to reproduce true to type in successive generations of asexual propagation via cuttings.

SUMMARY

The following are the most outstanding and distinguishing characteristics of this new variety when grown under normal horticultural practices in Stuttgart, Germany.

1. Yellow flower with red veins and a red magenta border; and
2. Mounding plant habit.

DESCRIPTION OF THE PHOTOGRAPH

This new *Calibrachoa* plant is illustrated by the accompanying photograph which shows a close-up of the whole plant.

The photograph is of a 12-week-old-plant grown in a greenhouse in Stuttgart, Germany in June 2022.

The colors shown are as true as can be reasonably obtained by conventional photographic procedures.

DESCRIPTION OF THE NEW VARIETY

The following detailed descriptions set forth the distinctive characteristics of 'KLECA23987'. The data which define these characteristics were collected from asexual reproductions carried out in Latina, Italy. Data was collected on 13-week old plants after transplant in Latina, Italy. Color references are to The R.H.S. Colour Chart of The Royal Horticultural Society of London (R.H.S.), 5$^{th}$ edition (2007).

Classification:
- *Family.*—Solanaceae.
- *Species.*—*Calibrachoa* sp.
- *Common name.*—*Calibrachoa.*

Parentage:
- *Female.*—'KLECA20803' (U.S. Plant Pat. No. 33,988).
- *Male.*—'KLECA22825' (unpatented).

Plant description:
- *Life cycle.*—Annual.
- *Form.*—Short-lived subshrub.
- *Habit.*—Mounding.
- *Height (from soil line to top of foliage).*—12.4 cm.
- *Spread.*—31.4 cm.

Propagation:
- *Type cuttings.*—Tip cutting.
- *Time to produce a rooted cutting.*—3 weeks.

Stems:
- *Stem color.*—RHS 144B.
- *Pubescence.*—Present.
- *Pubescence color.*—RHS 155A.
- *Stem diameter.*—0.12 cm.
- *Stem length.*—From soil line to first node: 1.3 cm. Total length: 15.7 cm.
- *Internode length.*—0.9 cm.

Leaves:
- *Arrangement.*—Alternate.

*Shape*.—Cuneate.
*Apex*.—Obtuse.
*Base*.—Acute.
*Margin*.—Ciliate.
*Surface pubescence*.—Present on both surfaces.
*Pubescence color*.—RHS 155A on both surfaces.
*Venation color*.—Upper surface: RHS 137B. Lower surface: RHS 137D.
*Length*.—3.1 cm (mature leaves).
*Width*.—1.3 cm (mature leaves).
*Color*.—Upper surface: RHS 137B. Lower surface: RHS 137D.
*Fragrance*.—Absent.

Flowers:
*Flowering habit*.—Single flower.
*Flower type*.—Single.
*Flowering requirements*.—A minimum of sun light is required, 9.5 hours.
*Duration of flowers*.—7 to 10 days.
*Corolla*.—Smooth.
*Shape*.—Funnel form.
*Fragrance*.—Absent.

Flower buds:
*Surface*.—Pubescent.
*Length*.—2.3 cm.
*Diameter*.—0.5 cm.
*Shape*.—Irregular to oblong.
*Color*.—RHS 60C (top buds), RHS 145C (base buds).

Peduncle:
*Length*.—2.1 cm.
*Diameter*.—Less than 0.1 cm.
*Color*.—RHS 144B.
*Texture*.—Pubescent.
*Anthocyanin*.—Absent.

Flower description:
*Flower depth*.—2.3 cm.
*Flower tube length*.—1.7 cm.
*Flower tube diameter*.—0.9 cm.
*Flower diameter*.—3.7 cm.
*Pedicel color*.—RHS 137A.
*Pedicel length*.—1.2 cm.

Calyx:
*Number*.—Five sepals for each calyx.
*Sepals*.—Shape: Ovate Apex: Obtuse Margin: Ciliate Length: 1.4 cm. Diameter. 0.35 cm. Sepal color: Upper surface: RHS 137A. Lower surface: RHS 137C.

Petals:
*Shape*.—Obcordate.
*Length*.—1.6 cm.
*Apex*.—Truncated.
*Margin*.—Entire.
*Base*.—Fuse in the tube.
*Pubescence*.—Absent.
*Lobing*.—Truncate.
*Lobe length*.—1.6 cm.
*Lobe width*.—1.8 cm.
*Color*.—Lobe color: Upper surface: RHS 8B main color and RHS 45B vein and border. Lower surface: RHS 8C main color and RHS 71B vein and border. Corolla tube color: Inner: RHS 12B. Outer: RHS 3C.
*Conspicuousness of the veins*.—Very strong.
*Fragrance*.—Absent.

Reproductive organs:
*Stamen number*.—5.
*Stamen color*.—Anther color: RHS 13B. Filament color: RHS 2C. Pollen color: RHS 12A.
*Placenta arrangement*.—Ovate.
*Pistil number*.—1.
*Pistil length*.—1.2 cm.
*Stigma color*.—RHS 144B.
*Style length*.—0.9 cm.
*Style color*.—RHS 145B.

Fruit/seed set: None observed.

Disease/insect resistance: No pests and disease were observed.

COMPARISON WITH PARENTAL LINES AND KNOWN VARIETY

'KLECA23987' is distinguished from its parents as described in Table 1 and Table 2:

TABLE 1

Comparison with Parental Lines

| Trait | Variety 'KLECA23987' | Female parent | Male Parent |
|---|---|---|---|
| Plant Habit | Mounding | Semi-mounding | Semi-trailing |
| Flower Pattern | Yellow flower with red veins (full) and red magenta border | Yellow flower with red eye | Yellow with red veins without red border |

'KLECA23987' is most similar to the *Calibrachoa* plant named 'KLECA15327' (U.S. Plant Pat. No. 28,390). Differences between the two varieties are described in Table 2:

TABLE 2

Comparison with Similar Variety

| Trait | Variety 'KLECA23987' | Commercial line 'KLECA15327' |
|---|---|---|
| Flower Pattern | Yellow flower with red veins (full) and red magenta border | Yellow flower without veins |
| Plant Habit | Mounding | Semi-trailing |

I claim:

1. A new and distinct cultivar of *Calibrachoa* Plant Named 'KLECA23987' as shown and described herein.

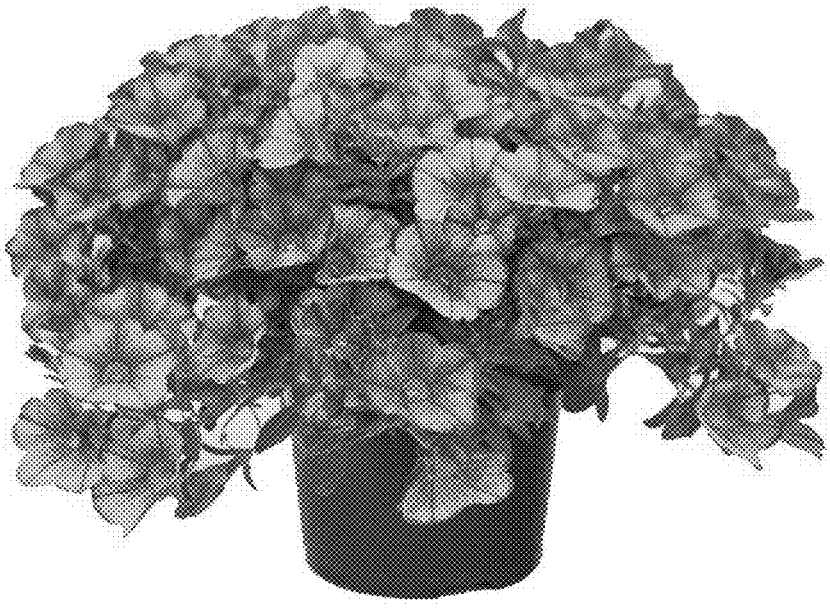

* * * * *